US009452296B2

(12) United States Patent
Forsell

(10) Patent No.: US 9,452,296 B2
(45) Date of Patent: Sep. 27, 2016

(54) METHOD AND SYSTEM FOR CONTROLLING SUPPLY OF ENERGY TO AN IMPLANTABLE MEDICAL DEVICE

(76) Inventor: Peter Forsell, Zug (CH)

(*) Notice: Subject to any disclaimer, the term of this patent is extended or adjusted under 35 U.S.C. 154(b) by 406 days.

(21) Appl. No.: 12/682,404

(22) PCT Filed: Oct. 10, 2008

(86) PCT No.: PCT/SE2008/000576
§ 371 (c)(1),
(2), (4) Date: Apr. 9, 2010

(87) PCT Pub. No.: WO2009/051539
PCT Pub. Date: Apr. 23, 2009

(65) Prior Publication Data
US 2010/0217353 A1    Aug. 26, 2010

Related U.S. Application Data

(60) Provisional application No. 60/960,832, filed on Oct. 16, 2007.

(51) Int. Cl.
| A61N 1/00 | (2006.01) |
| A61N 1/378 | (2006.01) |
| H02J 5/00 | (2016.01) |
| H02J 7/02 | (2016.01) |

(52) U.S. Cl.
CPC .............. *A61N 1/3787* (2013.01); *H02J 5/005* (2013.01); *A61F 2250/0001* (2013.01); *H02J 7/025* (2013.01)

(58) Field of Classification Search
CPC .............. A61F 2250/0001; A61N 1/3787; H02J 5/005
USPC .......................................... 607/31, 32, 61, 60
See application file for complete search history.

(56) References Cited

U.S. PATENT DOCUMENTS

| 3,942,535 A | 3/1976 | Schulman |
| 4,679,560 A | 7/1987 | Galbraith |
| 5,995,874 A * | 11/1999 | Borza ............................ 607/61 |

(Continued)

FOREIGN PATENT DOCUMENTS

| EP | 1 609 501 | 12/2005 |
| WO | 98/11942 | 3/1998 |
| WO | 01/28629 | 4/2001 |

OTHER PUBLICATIONS

International Search Report for PCT/SE2008/000576, mailed Feb. 5, 2009.

*Primary Examiner* — Niketa Patel
*Assistant Examiner* — Lindsey G Hankins

(57) ABSTRACT

A method and system for supplying energy to an electrically operable, medical device (100) implanted in ' a patient. Wireless energy is transferred from an external energy source (104) located outside the patient to an internal energy receiver (102) located inside the patient and connected to the medical device. An internal control unit (108) determines an amount of energy currently required for the operation of said medical device. A control signal is transmitted to the external energy source, reflecting the required amount of energy. An external control unit (106) controls the amount of transferred energy in response to the control signal, by adjusting the energy transfer efficiency from the external energy source to the internal energy receiver. The energy transfer efficiency is adjusted by adjusting the position of a primary coil, serving as the external energy source, relative to an implanted secondary coil, serving as the internal energy source.

22 Claims, 4 Drawing Sheets

(56) References Cited

U.S. PATENT DOCUMENTS

| | | | |
|---|---|---|---|
| 2003/0114905 A1* | 6/2003 | Kuzma | 607/116 |
| 2004/0039423 A1 | 2/2004 | Dolgin | |
| 2004/0250820 A1 | 12/2004 | Forsell | |
| 2005/0075697 A1 | 4/2005 | Olson et al. | |
| 2005/0228209 A1* | 10/2005 | Schneider et al. | 600/13 |
| 2007/0279020 A1* | 12/2007 | Mozzi et al. | 323/265 |

* cited by examiner

METHOD AND SYSTEM FOR CONTROLLING SUPPLY OF ENERGY TO AN IMPLANTABLE MEDICAL DEVICE

This application is the U.S. national phase of International Application No. PCT/SE2008/000576, filed 10 Oct. 2008, which designated the U.S. and claims priority to U.S. application Ser. No(s). 60/960,832, filed 16 Oct. 2007, the entire contents of each of which are hereby incorporated by reference.

TECHNICAL FIELD

The present invention relates generally to a method and system for supplying wireless energy to a medical device implanted in a patient. In particular, the invention is concerned with controlling the amount of energy transferred from an energy source outside the patient to an energy receiver inside the patient.

BACKGROUND

Medical devices designed to be implanted in a patient's body are typically operated by means of electrical power. Such medical devices include electrical and mechanical stimulators, motors, pumps, etc, which are designed to support or stimulate various body functions. Electrical power can be supplied to such an implanted medical device from a likewise implanted battery or, more preferably, from an external energy source that can supply any needed amount of electrical power more or less continuously without requiring repeated surgical operations.

An external energy source may be placed just beneath the patient's skin in the vicinity of the implanted device. So-called TET (Transcutaneous Energy Transfer) devices are known that can transfer wireless energy to an internal energy receiver which is located inside the patient and connected to the medical device for supplying received energy thereto. Thereby, no leads or the like penetrating the skin need to be used for connecting the medical device to an external energy source, such as a battery.

A TET device typically comprises an external energy source including a primary coil adapted to inductively transfer any amount of wireless energy, by inducing voltage in a secondary coil of an internal energy receiver which is implanted preferably just beneath the skin of a patient. The highest transfer efficiency is obtained when the primary coil is positioned close to the skin adjacent to and in alignment with the secondary coil, i.e. when a symmetry axis of the primary coil is parallel to that of the secondary coil.

Typically, the amount of energy required to operate an implanted medical device may vary over time depending on the operational characteristics of the device. For example, the device may be designed to switch on and off at certain intervals, or otherwise change its behaviour, in order to provide a suitable electrical or mechanical stimulation, or the like. Such operational variations will naturally result in corresponding variations with respect to the amount of required energy.

Furthermore, the position of the primary coil relative to the implanted secondary coil is a factor that affects the efficiency of the energy transfer, which highly depends on the distance between the coils and the relative angle between the coils. Initially, during set-up of a TET-system, it may be difficult to find an optimal position of the primary coil, and to maintain it in that position. During operation of the medical device, the patient's movements will typically change the relative spacing of the two coils such that the transfer efficiency greatly varies. Hence, changes in coil spacing result in a corresponding variation of the induced voltage.

If the transfer efficiency becomes low, the amount of energy supplied to the medical device may be insufficient for operating the device, so that its action must be momentarily stopped, naturally disturbing the intended operation of the device. Although this situation is more likely to occur when large amounts of power are to be transferred for supplying sufficient energy to an implant, it can be regarded as a general problem.

On the other hand, the energy supplied to the medical device may also increase drastically, if the relative positions of the coils change in a way that unintentionally increases the transfer efficiency. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the primary coil to the secondary coil, the temperature of the implant will increase, which may damage the surrounding tissue or otherwise have a negative effect on body functions. It is therefore highly desirable to always supply the right amount of energy to an implanted medical device during operation.

Methods are known for controlling the amount of transferred energy in response to measured conditions in the receiving implant. For example, U.S. Pat. No. 5,995,874 discloses a TET system in which the amount of transmitted energy from a primary coil is controlled in response to an indication of measured characteristics of a secondary coil, such as load current and voltage. The transmitted energy can be controlled by varying the current and voltage in the primary coil, transmission frequency or coil dimensions. In particular, a change is effected in the saturation point of the magnetic field between the coils, in order to adjust the power transfer efficiency. However, it is not likely that this solution works well in practice, since a saturation point in the human tissue would hardly occur, given the magnetic field levels that are possible to use. Moreover, if the energy transmission must be increased considerably, e.g. to compensate for losses due to variations in alignment and/or spacing between the coils, the relatively high radiation generated may be damaging or unhealthy or unpleasant to the patient, as is well known.

An effective solution is needed for accurately controlling the amount of transferred energy to an implanted medical device, where the correct amount of energy is always supplied to the device for proper operation thereof. In particular, excessive energy transfer resulting in raised temperature at the medical device, and/or power surges should be avoided. Furthermore, the transmitted electromagnetic energy should be kept at a minimum, in order to avoid tissue damages and other unhealthy or unpleasant consequences for the patient.

SUMMARY

The object of the present invention is to reduce or eliminate the problems outlined above. This object and others are obtained by providing a method and a system for supplying energy to an electrically operable medical device implanted in a patient, according to the attached independent claims.

According to one aspect, a method is provided where wireless energy is transferred from an external energy source located outside the patient to an internal energy receiver located inside the patient. The internal energy receiver is connected to the medical device for directly or indirectly supplying received energy thereto. First, an amount of energy is determined currently required for the operation of said medical device. Then, a control signal reflecting said required amount of energy, is transmitted to the external energy source, and the amount of transferred energy is controlled in response to the control signal by adjusting the energy transfer efficiency from the external energy source to the internal energy receiver.

According to another aspect, a system is provided comprising an external energy source adapted to transfer wireless energy from a position close to the skin of said patient to an internal energy receiver located inside the patient. The internal energy receiver is connected to the medical device for directly or indirectly supplying received energy thereto. The system further comprises an internal control unit adapted to determine an amount of energy currently required for the operation of said medical device, means for transmitting a control signal reflecting the required amount of energy, an external control unit adapted to control the amount of transferred energy in response to receiving the control signal, and means for adjusting the energy transfer efficiency from said external energy source to said internal energy receiver, as controlled by the external control unit.

The method and system may be implemented according to different exemplary embodiments and features as follows.

The external energy source may comprise a primary coil for transferring wireless energy inductively to a secondary coil in the internal energy receiver. The external control unit may control the adjusting means to adjust the position of the primary coil relative to the secondary coil, as controlled by the external control unit the adjusting means may include at least one position adjusting motor mechanically connected to the primary coil.

The position adjusting motor may include a position sensor for providing position information to the external control unit. A housing may enclose the position adjusting motor and the primary coil, to allow free movements of the primary coil.

The position adjusting motor may further include at least one distance adjusting motor for adjusting the distance between the primary coil and the secondary coil. The distance adjusting motor may include a distance adjusting linear motor for displacing the primary coil in a first direction substantially perpendicular to the skin of the patient. The distance adjusting motor may then include a first distance adjusting rotation motor for displacing the primary coil in a second direction substantially parallel to the patient's skin, by turning the primary coil around a first distance adjustment axis. The distance adjusting motor may also include a second distance adjusting rotation motor for displacing the primary coil in the second direction, by turning the primary coil around a second distance adjustment axis which is substantially parallel to but separate from the first distance adjustment axis.

Alternatively, the distance adjusting motor may include at least one angle adjusting motor for adjusting the angle between the primary coil and the secondary coil. In that case, the primary coil may comprise a helical winding around a symmetry axis, and the angle adjusting motor adjusts the angle by turning the symmetry axis of the primary coil relative to a corresponding symmetry axis of the secondary coil. The angle adjusting motor may also include a first angle adjusting motor for turning the primary coil around a first angle adjustment axis. The first angle adjustment axis may be substantially parallel to the patient's skin, and the first angle adjusting motor will then turn the primary coil in a first plane substantially perpendicular to the patient's skin. The first angle adjusting motor may be a linear motor or a rotation motor.

The angle adjusting motor may also include a second angle adjusting motor for turning the primary coil around a second angle adjustment axis perpendicular to the first angle adjustment axis. The second angle adjustment axis may be substantially parallel to the skin of said patient, and the second angle adjusting motor will then turn the primary coil in a second plane substantially perpendicular to the patient's skin and substantially perpendicular to the first plane. The second angle adjusting motor may be a linear motor or a rotation motor.

The position adjusting means may further include a first ring member inside which the primary coil is mounted by means of opposite first rotation bearings coaxial with the second angle adjustment axis, and a second ring member inside which the first ring member is mounted by means of opposite second rotation bearings coaxial with the first angle adjustment axis, such that said primary coil can be tilted in any direction as a gyro.

The control signal may reflect the difference or ratio between the energy received by the internal energy receiver and the required amount of energy.

The external control unit may control the adjusting means to decrease the energy transfer efficiency if the received energy is greater than the required amount of energy. The external control unit may also control the adjusting means to increase the energy transfer efficiency if the received energy is less than the required amount of energy.

Further, the control signal may reflect an amount of energy per time unit currently required for directly operating the medical device. In that case, the control signal may reflect the required amount of energy as an energy balance between the received energy and the energy consumed by the medical device.

The incoming energy may be stored in an energy storing device, such as a battery or a capacitor. Measuring means may measure at least one characteristic and/or parameter of the energy storing device, and determining and storing means may determine and store the current state of the energy storing device. The measuring means may measure the characteristic and/or parameter of the energy storing device on a regular basis for updating the stored state of the energy storing device.

Controlling means may control the amount of transferred energy based on measurements made on at least one of: the medical device, the patient, and an energy storing device.

BRIEF DESCRIPTION OF THE DRAWINGS

The present invention will now be described in more detail and with reference to the accompanying drawings, in which.

DETAILED DESCRIPTION

Figure 1:
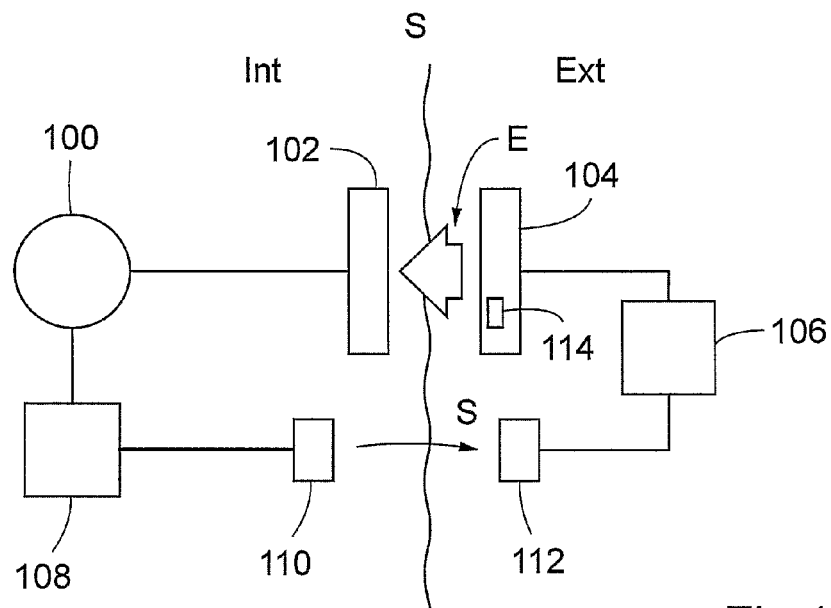
FIG. 1 is a schematic block diagram illustrating an arrangement for supplying an accurate amount of energy to an electrically operable medical device.

In FIG. 1, an arrangement is schematically illustrated for supplying an accurate amount of energy to an electrically operable medical device 100 implanted in a patient, whose skin is indicated by a vertical line S separating the interior (Int) of the patient from the exterior (Ext). The medical device 100 is connected to an internal energy receiver 102, likewise located inside the patient, preferably just beneath the skin S. Generally speaking, the energy receiver 102 may be placed in the abdomen, thorax, muscle fascia (e.g. in the abdominal wall), subcutaneously, or at any other suitable location. The energy receiver 102 is adapted to receive wireless energy E transmitted from an external energy source 104 located outside the skin S in the vicinity of the energy receiver 102.

As is well-known in the art, the wireless energy E may generally be transferred by means of any suitable TET-device, such as a device including a primary coil arranged in the energy source 104 and an adjacent secondary coil arranged in the energy receiver 102. When an electric current is fed through the primary coil, energy in the form of a voltage is induced in the secondary coil which can be used to operate a medical device, preferably after storing the incoming energy in an energy storing device or accumulator, such as a battery or a capacitor. However, the present invention is generally not limited to any particular energy transfer technique, TET-devices or energy storing devices.

The amount of transferred energy can be regulated by means of an external control unit 106 controlling the energy source 104. It is desirable to accurately control the amount of transferred energy, for reasons discussed in the background section above. In order to transfer the correct amount of energy, an amount of energy currently required is determined by means of an internal control unit 108 connected to the medical device 100. The control unit 108 may thus be arranged to receive various measurements obtained by suitable sensors or the like, not shown, measuring certain characteristics of the medical device 100, somehow reflecting the required amount of energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by, e.g., body temperature, heartbeats and breathing.

Furthermore, an energy storing device or accumulator, not shown here, may also be connected to the energy receiver 102 for accumulating received energy for later use by the medical device 100. Alternatively or additionally, characteristics of such an energy storing device, also reflecting the required amount of energy, may be measured as well. The energy storing device may be a battery, and the measured characteristics may be related to the current state of the battery, such as voltage, temperature, etc. In order to provide sufficient voltage and current to the medical device 100, and also to avoid overheating, it is clearly understood that the battery should be charged optimally by receiving a correct amount of energy from the energy receiver 102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 108 is adapted to determine the currently required amount of energy, (either energy per time unit or accumulated energy) based on measurements made by the above-mentioned sensors or measuring devices on the medical device 100, or the patient, or an energy storing device if used, or any combination thereof. The internal control unit 108 is further connected to an internal signal transmitter 110, arranged to transmit a control signal reflecting the determined required amount of energy, to an external signal receiver 112 connected to the external control unit 106. The amount of energy transmitted from the energy source 104 may then be regulated in response to the received control signal.

The internal signal transmitter 110 and the external signal receiver 112 may be implemented as separate units using suitable signal transfer means, such as radio, IR (Infrared) or ultrasonic signals. Alternatively, the signal transmitter 110 and the signal receiver 112 may be integrated in the internal energy receiver 102 and the energy source 104, respectively, so as to convey control signals in a reverse direction relative to the energy transfer, basically using the same transmission technique. The energy source 104 may further include one or more position sensors, generally illustrated as a single sensor 114, the purpose of which will be described later. The position sensor 114 is adapted to detect the current position of the energy source 104 relative some suitable reference point, such as a housing in which the energy source 104 is movably mounted.

To conclude, the energy supply arrangement illustrated in FIG. 1 may operate basically in the following manner. A currently required amount of energy is first determined by the internal control unit 108. A control signal S reflecting the required amount of energy is also created by the internal control unit 108, and the control signal S is transmitted from the signal transmitter 110 to the signal receiver 112. The amount of energy emitted from the energy source 104 can then be regulated by the external control unit 106, in response to the received control signal S. This process may be repeated intermittently at certain intervals during ongoing energy transfer, or may be executed on a more or less continuous basis during the energy transfer.

The amount of transferred energy can generally be regulated by adjusting various transmission parameters in the energy source 104, such as amplitude, frequency and pulse characteristics. In the present solution, however, the amount of transferred energy is specifically regulated by adjusting the energy transfer efficiency between the external energy source 104 and the internal energy receiver 102. Such adjustment of energy transfer efficiency can be made alone or in combination with any additional adjustments of parameters of the emitted transmission signal, in response to the received control signal S.

Depending on the received control signal, the energy transfer efficiency is adjusted to decrease the energy transfer efficiency if the received energy is greater than the required amount of energy. On the other hand, the energy transfer efficiency is adjusted to increase the energy transfer efficiency if the received energy is less than said required amount of energy.

The present invention will be exemplified below in the case where wireless energy is inductively transferred from a primary coil in an energy source to a secondary coil in an energy receiver, as explained above. Each coil has a helical shape with a central symmetry axis. The energy transfer efficiency is preferably adjusted by adjusting the position of the primary coil relative to the secondary coil, which is in a more or less fixed position inside the patient's body. However, the position of the secondary coil may change over time, e.g. due to body movements, such that the position of the primary coil needs to be adjusted accordingly for compensation.

Figure 2:
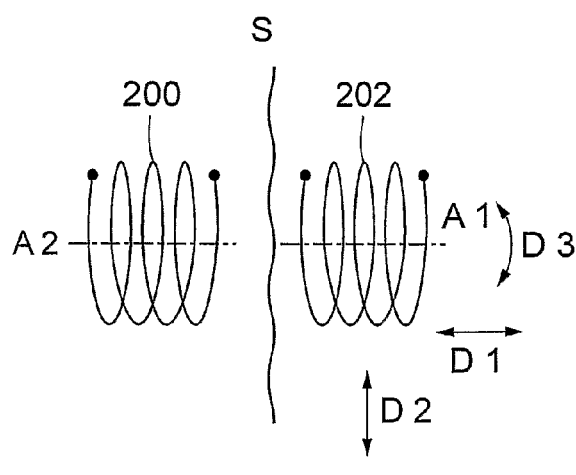
FIG. 2 is a simplified diagram of a primary coil and a secondary coil of a TET system according to one embodiment.

FIG. 2 illustrates an embodiment where an energy receiver is arranged in the patient such that a secondary coil 200 is located beneath the skin S, having its symmetry axis A2 oriented substantially perpendicular to the skin S. When an energy transfer is to be performed, a primary coil 202 of an energy source is first placed next to the skin S, preferably in approximate alignment with the secondary coil 200 such that its symmetry axis A1 substantially coincide with symmetry axis A2, as shown in the figure. In this initial relative position, the energy transfer efficiency will be relatively great when an electric current is fed through the primary coil 202. In order to adjust the energy transfer efficiency, the position of the primary coil can be adjusted basically in at least one of three different ways.

Firstly, the distance between the primary and secondary coils 202, 200 may be adjusted by displacing said primary coil along a first direction D1 substantially perpendicular to the skin S, i.e. to the right or to the left in the figure. Thereby, the symmetry axis of the respective coils will remain coincided when the primary coil is moved to and fro in this direction D1.

Secondly, the distance between the primary and secondary coils 202, 200 may be adjusted by displacing the primary coil along a second direction D2 substantially parallel to the skin S, i.e. upwards or downwards in the figure. Thereby, the symmetry axis of the respective coils will be mutually displaced when the primary coil is moved to and fro in this direction D2.

It will be readily understood that for both directions D1 and D2, a greater mutual distance between the coils will result in less transfer efficiency, and vice versa. For example, a selected first reference point at the primary coil may be displaced relative to a selected second reference point at the secondary coil. For this purpose, any points on the coils, e.g., symmetry mid-points or weight mid-points, may be selected as the first and second reference points of the primary and secondary coils, respectively.

Thirdly, the position of the primary coil can be adjusted by turning the symmetry axis A1 of the primary coil 202 relative to the symmetry axis A2 of the secondary coil 200, in a turning third direction D3. The turning direction D3 of the primary coil may be oriented in any plane perpendicular to the skin S. Thereby, the angle between the symmetry axis of the respective coils will be changed when the primary coil is moved to and fro in this direction D3. Thus, a greater angle between the coils will result in less transfer efficiency, and vice versa, the angle being zero when the symmetry axes A1, A2 are parallel.

Figure 3:
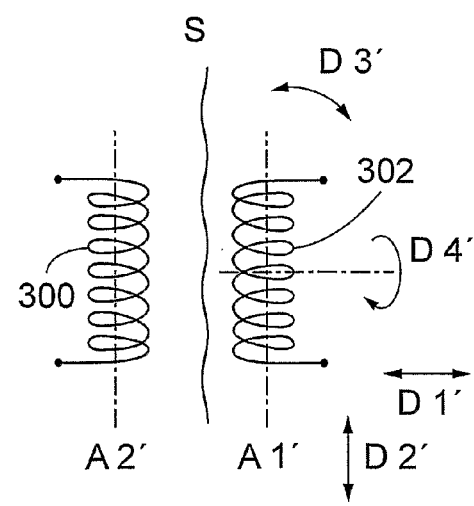
FIG. 3 is a simplified diagram of a primary coil and a secondary coil of a TET system according to another embodiment.

FIG. 3 illustrates another embodiment where an energy receiver is arranged in the patient such that a secondary coil 300 is located beneath the skin S, having its symmetry axis A2' oriented substantially parallel to the skin S. When an energy transfer is to be conducted, a primary coil 302 of an energy source is first placed preferably next to the skin S adjacent to the secondary coil 300, as shown in the figure, such that its symmetry axis A1' is substantially parallel to symmetry axis A2'. In this initial relative position, the energy transfer efficiency will be relatively great when a current is fed to the primary coil 302. In order to adjust the energy transfer efficiency, the position of the primary coil 302 can be adjusted basically in at least one of four different ways.

Firstly and secondly, the primary coil 302 may be displaced along a first direction D1 substantially perpendicular to the skin S, and along a second direction D2 substantially parallel to the skin S, respectively, in the same manner as in the embodiment illustrated in FIG. 2.

Thirdly, the symmetry axis A1' of the primary coil 302 may be turned in a third turning direction D3' around an axis perpendicular to the coil 302 but parallel to the skin S.

Fourthly, the symmetry axis A1' of the primary coil 302 may also be turned in a fourth turning direction D4' around an axis perpendicular to the skin S. In both cases, the angle between the symmetry axis of the respective coils will be changed when the primary coil 302 is turned to and fro in either direction D3' and D4', respectively. As in FIG. 3, a greater angle between the coils will result in less transfer efficiency, and vice versa, the angle being zero when the symmetry axes A1', A2' are parallel.

Figure 4A:
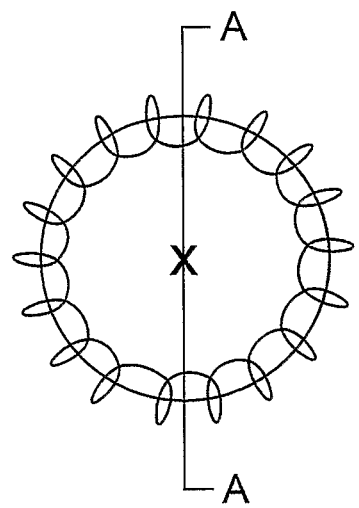
FIG. 4 is a simplified diagram of a primary coil and a secondary coil of a TET system according to yet another embodiment.
Figure 4B:
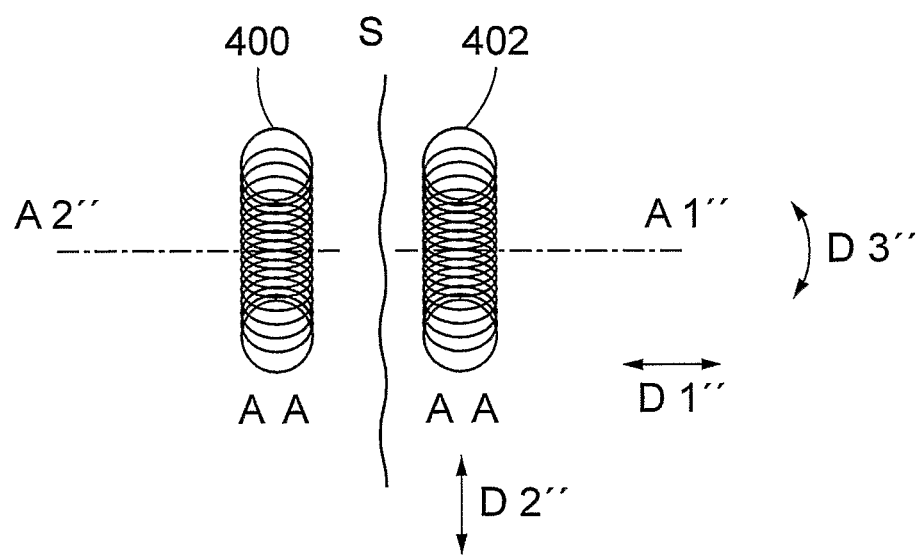

FIG. 4 illustrates yet another embodiment where the primary and secondary coils 400 and 402, respectively, are toroid-shaped with their symmetry axes A1", A2" oriented substantially perpendicular to the skin S. FIG. 4a is a top view of such a toroid-shaped coil, its symmetry axis being the normal at x. The position of the primary coil 402 can be adjusted basically in at least one of three different directions D1", D2" and D3" which totally correspond to the directions D1, D2 and D3 in FIG. 2, and therefore need not be explained further.

In all the different coil configurations shown in FIGS. 2-4, the described adjustment directions may of course be used individually or combined in any manner, within the scope of the present invention.

Figure 5:
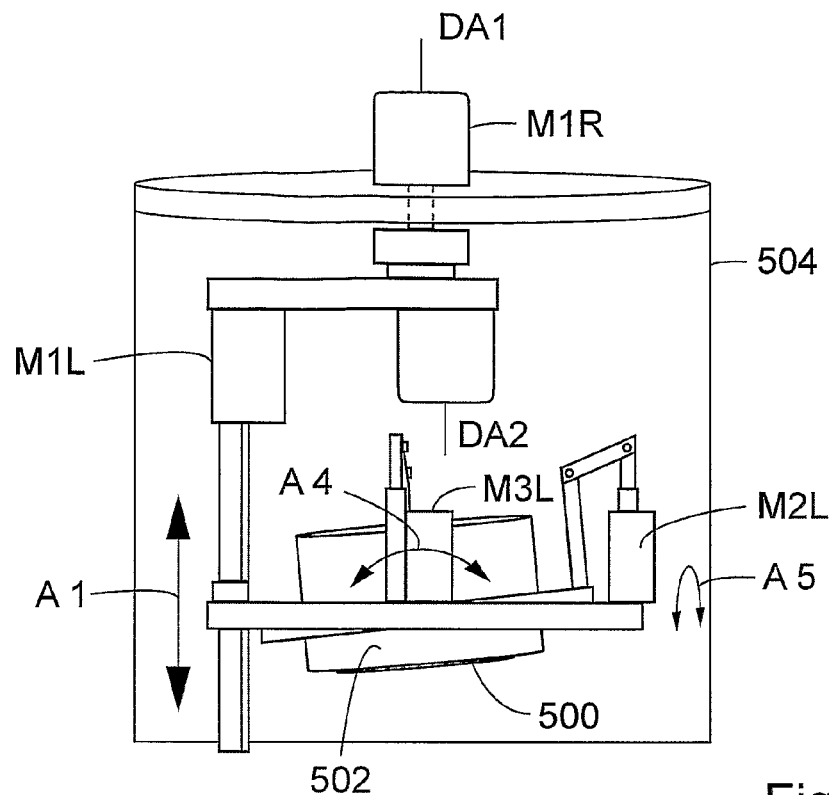
FIG. 5 is a perspective side view of a coil displacement unit according to one embodiment.
Figure 6:
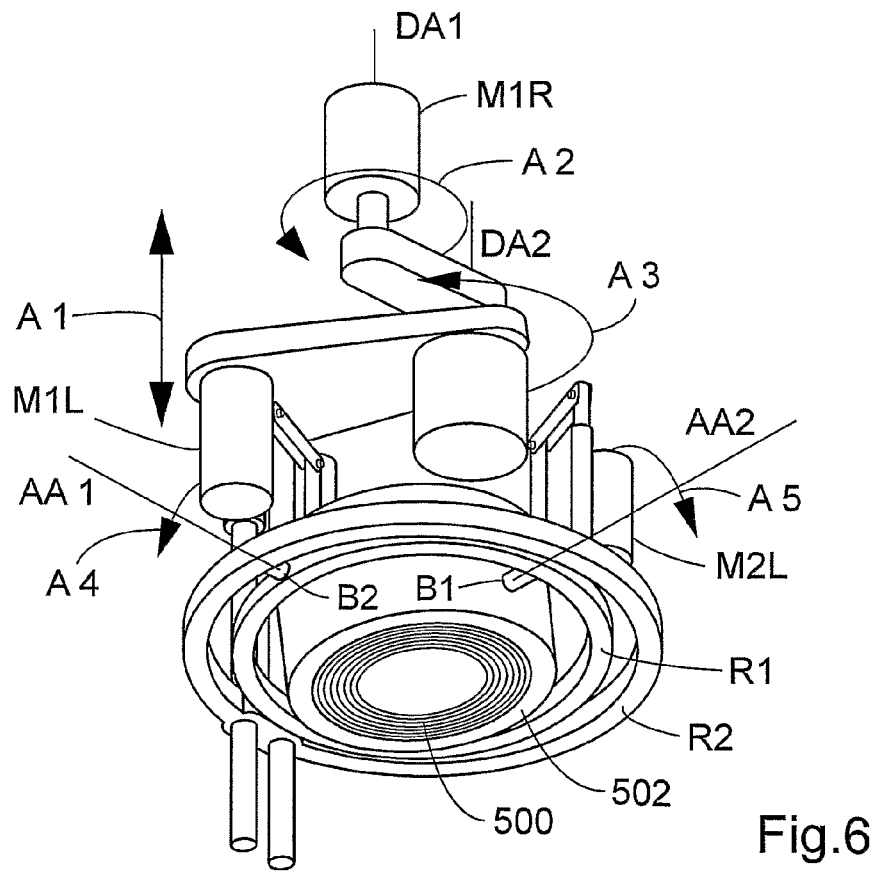
FIG. 6 is a perspective side view slightly from below of the coil displacement unit of FIG. 5.
Figure 7:
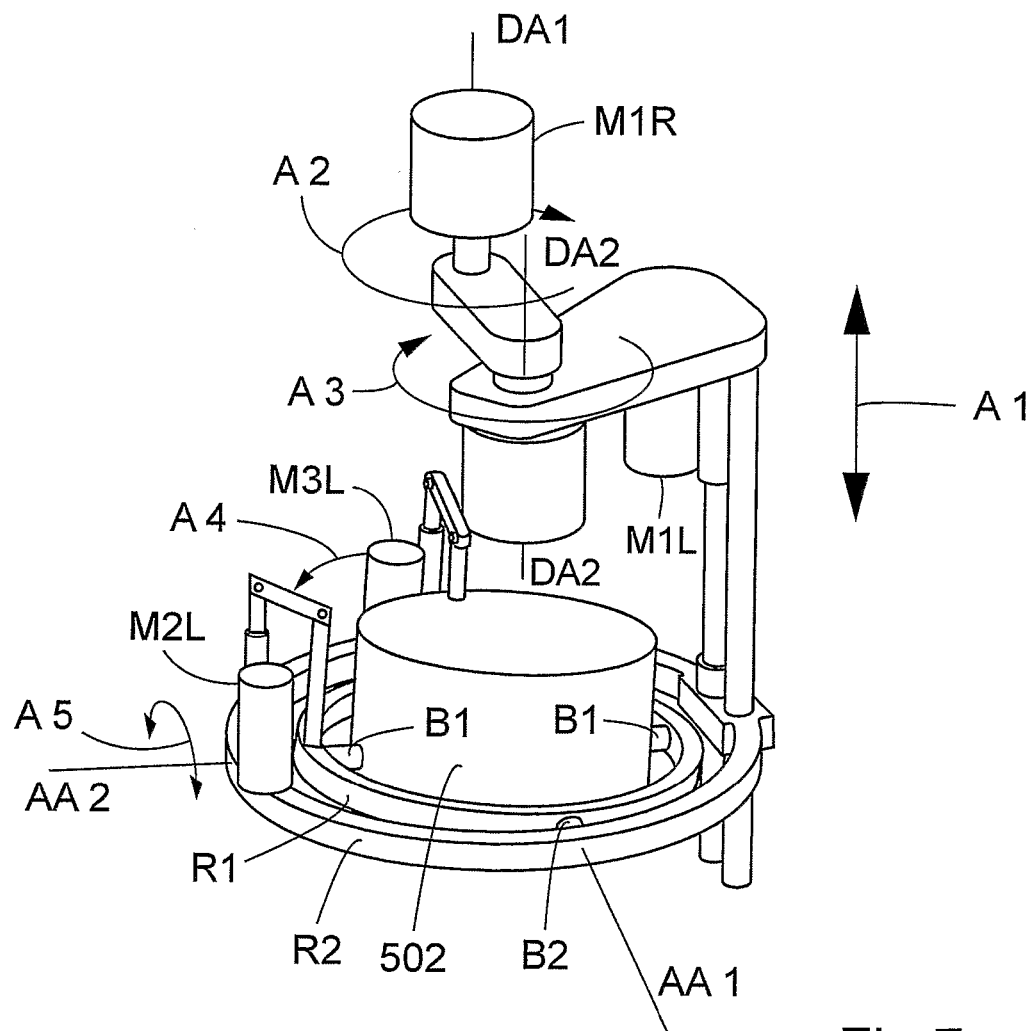
FIG. 7 is a perspective side view slightly from above of the coil displacement unit of FIG. 5.

FIG. 5-7 illustrates an embodiment of a coil displacement unit configured to displace a primary coil 500 in a plurality of different directions relative to a secondary coil, not shown. The coil 500 is mounted in a support cylinder 502 which is suspended in a movable manner, as will be described below.

The coil displacement unit comprises plural position adjusting motors mechanically connected to the support cylinder 502 and thereby also to the primary coil 500. Each position adjusting motor further includes some type of position sensor, not shown in FIGS. 5-7 but schematically indicated as 114 in FIG. 1, adapted to provide position information to a processor, likewise not shown, which corresponds to the external control unit 106 of FIG. 1. The processor is adapted to control the movement of the primary coil 500, based on a received control signal, corresponding to the control signal S in FIG. 1, and on position information from the position sensors.

The coil displacement unit further comprises a housing 504, not shown in FIGS. 5 and 6, supporting and enclosing the position adjusting motors and the primary coil, to allow free movements of the primary coil.

The coil displacement unit comprises a distance adjusting linear motor M1L for displacing the primary coil in a first direction substantially perpendicular to the skin of the patient, as indicated by arrow A1.

The coil displacement unit further comprises a first distance adjusting rotation motor M1R adapted to displace the primary coil in a second direction substantially parallel to the skin of said patient, by turning the primary coil around a first distance adjustment axis DA1, as indicated by arrow A2.

The coil displacement unit further comprises a second distance adjusting rotation motor M2R adapted to displace the primary coil in the second direction, by turning the primary coil around a second distance adjustment axis DA2 which is substantially parallel to but separate from the first distance adjustment axis DA1, as indicated by arrow A3.

The coil displacement unit further comprises a first angle adjusting linear motor M2L adapted to turn the primary coil around a first angle adjustment axis AA1, as indicated by arrow A4. The first angle adjustment axis is substantially parallel to the skin of said patient, and the motor M2L is adapted to turn the primary coil in a first plane substantially perpendicular to the skin of said patient.

The coil displacement unit further comprises a second angle adjusting linear motor M3L adapted to turn the primary coil around a second angle adjustment axis AA2 perpendicular to the first angle adjustment axis AA3. The second angle adjustment axis AA2 is substantially parallel to the skin of the patient, and the motor M3L is adapted to turn the primary coil in a second plane substantially perpendicular to the skin of the patient and substantially perpendicular to the first plane.

The coil displacement unit further comprises a first ring member R1 inside which the primary coil is mounted by means of opposite first rotation bearings B1 coaxial with the second angle adjustment axis AA2, and a second ring member R2 inside which the first ring member R1 is mounted by means of opposite second rotation bearings B2 coaxial with the first angle adjustment axis AA1, such that the primary coil 500 can be tilted in any direction as a gyro.

While the invention has been described with reference to specific exemplary embodiments, the description is only intended to illustrate the inventive concept and should not be taken as limiting the scope of the invention. Various alternatives, modifications and equivalents may be used without departing from the invention, which is defined by the appended claims.

The invention claimed is:

1. A method of supplying energy to an electrically operable medical device implanted in a patient, Wherein wireless energy is transferred from an external energy source located outside the patient to an internal energy receiver located inside the patient, said internal energy receiver being connected to said medical device for directly or indirectly supplying received energy thereto, the method comprising the following steps:
   determining an amount of energy currently required for the operation of said medical device,
   transmitting, to said external energy source, a control siwlal from said medical. device or internal energy receiver reflecting said required amount of energy,
   transferring inductively from a primary coil in said external energy source to a secondary coil in said internal energy receiver,
   controlling the amount of transferred energy using an external control unit to in response to said control signal accurately controlling the amount of transferred energy to the implanted medical device, by adjusting the energy transfer efficiency from said external energy source to said internal energy receiver, where the correct amount of energy is always supplied to the medical device for proper operation thereof,
   repeatedly adjusting the energy transfer efficiency by adjusting the position of said primary coil relative to said secondary coil, and
   displacing the primary coil in at least one of a plurality of different directions relative to said secondary coil,
   using a coil displacement unit configured to displace the primary coil in the plurality of different directions.

2. A method according to claim 1, wherein said position is adjusted by adjusting the distance between said primary coil and said secondary coil by adjusting the position of the primary coil in the coil displacement unit.

3. A method according to claim 2, wherein said distance is adjusted by displacing a first reference point at said primary coil relative to a second reference point at said secondary coil.

4. A method according to claim 3, wherein said first and second reference points are the weight or symmetry centres of said primary and secondary coils, respectively.

5. A method according to claim 2, wherein said distance is adjusted by displacing said primary coil in a first direction substantially perpendicular to the skin of said patient.

6. A. method according to claim 5, wherein said distance is adjusted by displacing said primary coil in a second direction substantially parallel to the skin of said patient.

7. A method according to claim 6, wherein said primary coil is displaced in said second direction circumferentially around a first distance adjustment axis which is substantially perpendicular to the skin of said patient.

8. A method according to claim 7, wherein said primary coil is displaced in said second direction circumferentially around a second distance adjustment axis which is substantially parallel to but separate from said first distance adjustment axis.

9. A method according to claim 1, wherein said position is adjusted by adjusting the angle between said primary coil and said secondary coil by adjusting the position of the primary coil in the coil displacement unit.

10. A method according to claim 9, wherein said primary and secondary coils each comprises a helical winding around a symmetry axis, and said angle is adjusted by turning the symmetry axis of said primary coil relative to the symmetry axis of said secondary coil.

11. A method according to claim 10, wherein said angle is adjusted by turning said primary coil around a first angle adjustment axis.

12. A method according to claim 11, wherein said first angle adjustment axis is substantially parallel to the skin of said patient, such that said primary coil is turned in a first plane substantially perpendicular to the skin of said patient.

13. A method according to claim 11, wherein said angle is adjusted by turning said primary coil around a second angle adjustnient axis substantially perpendicular to said first angle adjustment axis.

14. A method according to claim 13, wherein said second angle adjustment axis is substantially parallel to the skin of said patient, such that said primary coil is turned in a second plane substantially perpendicular to the skin of said patient and substantially perpendicular to said first plane.

15. A method according to claim 1, wherein said control signal reflects the difference or ratio between the energy received by said internal energy receiver and at least one of; said required amount of energy, and energy consumed by said medical device.

16. A method according to claim 15. wherein the energy transfer efficiency is increased if said received energy is less than said consumed of energy and increased if said received energy is less than said consumed energy.

17. A method according to claim 16, wherein an amount of currently consumed energy per time unit is determined for directly operating the medical device.

18. A method according to claim 15, wherein an amount of currently required or consumed energy is determined for storing the incoming energy in an energy storing device, wherein at least one characteristic, parameter, or characteristic and parameter of the energy storing device is measured.

19. A method according to claim 1, wherein the energy transfer efficiency is decreased if said received energy is greater than said required amount of energy and increased if said received energy is less than said required amount of energy.

20. A method according to claim 1, wherein an amount of currently required energy per time unit is determined for directly operating the medical device.

21. A method according to claim 1, wherein the position of said primary coil relative to said secondary coil is repeated intermittently.

22. A method according to claim 1, wherein the position of said primary coil relative to said secondary coil is repeated continuously.

* * * * *